United States Patent
Han et al.

(10) Patent No.: US 10,760,051 B2
(45) Date of Patent: Sep. 1, 2020

(54) PROCESS FOR PREPARING ASTROCYTES

(71) Applicant: Korea Research Institute of Bioscience and Biotechnology, Daejeon (KR)

(72) Inventors: Baek Soo Han, Daejeon (KR); Sang Chul Lee, Daejeon (KR); Kwang-Hee Bae, Daejeon (KR); Cheonok Lee, Daejeon (KR); Won Kon Kim, Daejeon (KR); Kyoung Jin Oh, Daejeon (KR)

(73) Assignee: Korea Research Institute of Bioscience and Biotechnology, Daejeon (KR)

( * ) Notice: Subject to any disclaimer, the term of this patent is extended or adjusted under 35 U.S.C. 154(b) by 203 days.

(21) Appl. No.: 15/506,626

(22) PCT Filed: Aug. 13, 2015

(86) PCT No.: PCT/KR2015/008482
§ 371 (c)(1),
(2) Date: Feb. 24, 2017

(87) PCT Pub. No.: WO2016/032152
PCT Pub. Date: Mar. 3, 2016

(65) Prior Publication Data
US 2017/0267971 A1    Sep. 21, 2017

(30) Foreign Application Priority Data
Aug. 25, 2014   (KR) .................. 10-2014-0110565

(51) Int. Cl.
*C12N 5/079*   (2010.01)
(52) U.S. Cl.
CPC ........ *C12N 5/0622* (2013.01); *C12N 2500/32* (2013.01); *C12N 2501/10* (2013.01); *C12N 2501/105* (2013.01); *C12N 2501/11* (2013.01); *C12N 2501/115* (2013.01); *C12N 2501/13* (2013.01); *C12N 2501/16* (2013.01); *C12N 2501/91* (2013.01); *C12N 2506/02* (2013.01)
(58) Field of Classification Search
None
See application file for complete search history.

(56) References Cited

U.S. PATENT DOCUMENTS

| 6,897,061 | B1 | 5/2005 | Salin-Nordstrom |
| 2010/0323444 | A1 | 12/2010 | Steindler et al. |
| 2012/0115229 | A1 | 5/2012 | Eithan et al. |

FOREIGN PATENT DOCUMENTS

| KR | 10-0495532 B1 | 6/2005 |
| KR | 10-0683199 B1 | 2/2007 |
| KR | 10-2007-0047836 A | 5/2007 |
| KR | 10-2014-0071512 A | 6/2014 |
| WO | WO 2004015077 | * 2/2004 |
| WO | WO 2005/003320 A2 | 1/2005 |

OTHER PUBLICATIONS

Shaltouki "Efficient Generation of Astrocytes from Human Pluripotent Stem Cells in Defined Conditions" stem cells 31:941-952 (Year: 2013).*
Hanna "B27 supplement" accessed from hannalabweb.weizmann.ac.il on May 15, 2019 (Year: 2016).*
ThermoFisher "B27 supplement (50x), serum free" accessed from thermofisher.com on May 15, 2019 (Year: 2019).*
Atossa Shaltouki, et al., "Efficient Generation of Astrocytes from Human Pluripotent Stem Cells in Defined Conditions", Stem Cells, 2013; 31; 941-952.
Andrew Chojnacki, et al., "Production of neurons, astrocytes and oligodendrocytes from mammalian CNS stem cells", Nature Protocol, Feb. 2008.
International Search Report in connection with PCT International Application No. PCT/KR2015/008482.
Office Action dated Mar. 8, 2017 by the Korean Intellectual Property Office in connection with related Korean Patent Application No. KR 10-2014-0110565.
A. Swistowski, et al. "Xeno-Free Defined Conditions for Culture of Human Embryonic Stem Cells, Neural Stem Cells and Dopaminergic Neurons Derived from Them", Stem Cells, 2013, vol. 31, pp. 941-952.

* cited by examiner

*Primary Examiner* — Adam Weidner
(74) *Attorney, Agent, or Firm* — John P. White; Gary J. Gershik; Cooper & Dunham LLP

(57) ABSTRACT

The present invention relates to a method for producing astrocytes comprising obtaining neural progenitor cells from stem cells so as to continuously produce astrocytes with high purity and same traits, followed by two steps of differentiating the neural progenitor cells into the astrocytes, and astrocytes produced therefrom. Since the method of preparing the astrocytes provided in the present invention enables not only production of the astrocytes with high purity and faster production of the astrocytes with same characteristics, but also rapid differentiation of the astrocytes using the neural progenitor cells when necessary, it can be widely used for effectively treating a patient with a disease which requires transplantation of the astrocytes.

6 Claims, 2 Drawing Sheets

PROCESS FOR PREPARING ASTROCYTES

CROSS-REFERENCE TO RELATED APPLICATION

This application is a § 371 national stage of PCT International Application No. PCT/KR2015/008482, filed Aug. 13, 2015, claiming priority to Korean Patent Application No. KR 10-2014-0110565, filed Aug. 25, 2014, the content of each of which is hereby incorporated by reference into the application.

TECHNICAL FIELD

The present invention relates to a method for producing astrocytes, more specifically to a method for producing astrocytes comprising forming neural progenitor cells from stem cells, followed by two steps of differentiating the neural progenitor cells into the astrocytes, and astrocytes produced therefrom.

BACKGROUND ART

As mammal neurons do not regenerate if damaged, neurodegenerative diseases such as stroke, Parkinson's disease, or Alzheimer's disease may occur when the neurons are damaged. Accordingly, treatments that can cure diseases due to neuronal death have been actively studied worldwide for a long time, but an adequate treatment has not yet been developed.

Recently, research has been actively carried out to develop a method for treating the neurons damaged by differentiating stem cells, which are pluripotent cells capable of differentiating into various cells, into neurons. As the stem cells can be differentiated into various cells, such method may be fundamental in treating a disease that induces tissue damage. However, as it is not easy to obtain the stem cells or differentiate the stem cells into desired cells, and as the possibility of the stem cells themselves being rejected by patients' immune system can be problematic, the method has not been used universally. However, a cranial nerve disease accompanied by neural damage is considered to be the most appropriate object for the treatment using the stem cells because unlike other tissues, there is little rejection by the immune system in the cranial nervous system tissue, thereby making it possible to expect long-term survival of transplanted cells when the cells are transplanted from outside.

Studies for developing a method for applying the stem cells to treatments of diseases such as stroke, Alzheimer's disease, Parkinson's disease, demyelinating disease, and spinal cord injury are actively under way. For example, International Publication No. WO 2005/003320 discloses a method for inducing the stem cells into neurons, comprising sequentially adding and culturing a basic fibroblast growth factor (bFGF), fibroblast growth factor 8, sonic hedgehog (SHH), and brain-derived neurotrophic factor (BDNF) and ultimately co-culturing with astrocytes. Korean Patent Application No. 10-0495532 discloses a method for differentiating mesenchymal stem cells into neurons by culturing in a culture medium comprising an epidermal growth factor (EGF) and hepatocyte growth factor (HGF) and for proliferating the neurons.

Astrocytes, also known as astroglia, which are a type of neurons, as main supporting cells of the nervous system, are known to play a role in aiding neuronal activities while appropriately eliminating neurotransmitters secreted by neurons and controlling ion concentrations in the brain. Recently, as astrocytes have been revealed to play certain roles, such as in synapse formation of neurons, regulation of synapse number, and synaptic plasticity, and in the onset of degenerative nervous system diseases as well as differentiation of neural stem cells into nerves, more active research has been carried out on whether the astrocytes can be used for treating or improving the neurodegenerative diseases by differentiation.

According to what has been reported so far, a method for differentiating from nerve stem cells into astrocytes via astrocyte progenitor cells (Korean Application Publication No. 10-2014-0071512) and a method of differentiating astrocytes using DMEM/F-12 comprising B-27™ medium supplement (Gibco Life Technologies Corporation, 3175 Staley Road, Grand Island N.Y. 14075, acquired by, and B-27™ medium supplement now distributed by, Thermo Fisher Scientific Inc., Waltham, Mass., USA), bFGF, and heparin (U.S. Pat. No. 6,897,061) are known. However, the astrocytes differentiated by the conventional method include other cells in addition to pure astrocytes, thereby causing a problem in that differentiation efficiency and purity of the astrocytes are low, and this problem has not yet been resolved.

DISCLOSURE

Technical Problem

The present inventors have made diligent research efforts in order to develop a method for producing astrocytes with high purity by differentiating stem cells. As a result, the present inventors have completed the present invention by confirming that rather than directly differentiating the stem cells into the astrocytes, astrocytes can be obtained with high purity by forming neural progenitor cells from the stem cells, followed by two steps of differentiation of the neural progenitor cells.

Technical Solution

An object of the present invention is to provide a method for producing astrocytes comprising forming neural progenitor cells from stem cells, followed by two steps of differentiation of the neural progenitor cells into astrocytes. Another object of the present invention is to provide astrocytes produced therefrom.

Advantageous Effects

Since the method for producing the astrocytes provided in the present invention enables not only production of the astrocytes with high purity and faster production of the astrocytes with same characteristics, but also rapid differentiation of the astrocytes using the neural progenitor cells when necessary, it can be widely used for effectively treating a patient with a disease which requires transplantation of the astrocytes.

BEST MODE

Figure 1:
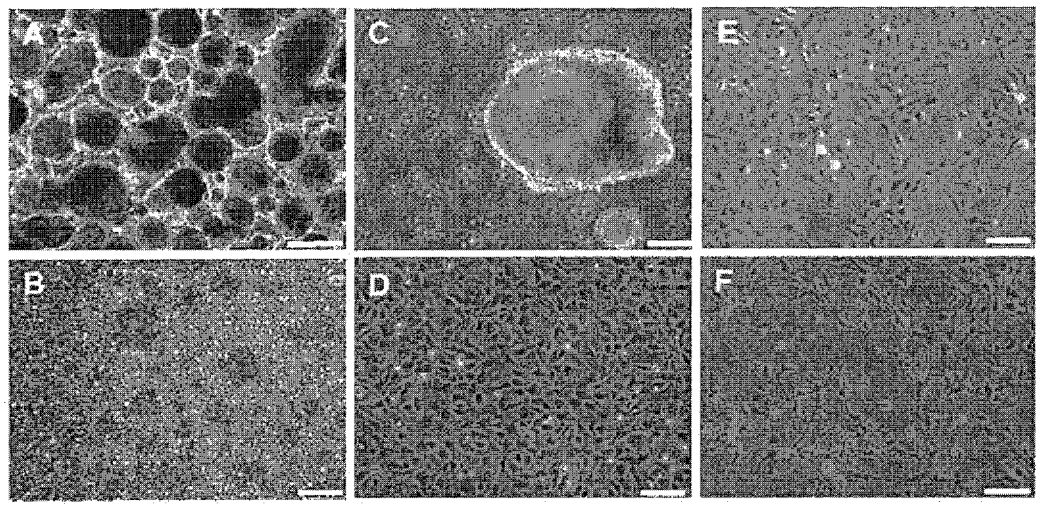
FIG. 1 is photomicrographs showing morphologies of (A) embryoid bodies, (B) rosettes, (C) neurospheres, (D) neural progenitor cells, (E) intermediate cells, and (F) astrocytes.

While conducting research in order to develop a method for producing the astrocytes with high purity by differentiating the stem cells, the present inventors focused on a method via neural progenitor cells. It was confirmed that the neural progenitor cells, unlike other neurons, may be cryopreserved, but may also be differentiated into the astrocytes with high purity, unlike stem cells, for which the purity of differentiated cells is difficult to control. Producing the astrocytes using such method is advantageous in that the astrocytes can be differentiated from the neural progenitor cells, thereby enabling a more rapid production of the astrocytes, in contrast to a conventional method for differentiating the astrocytes from the stem cells. Additionally, it was also confirmed that differentiating the neural progenitor cells into astrocytes in two steps, rather than in a single step, decreases a proportion of differentiation byproduct cells other than the astrocytes differentiated from the neural progenitor cells significantly, and therefore, an effect of an increase in efficiency of differentiation into the astrocytes may be exhibited. Such effect was never reported in the conventional technique using known methods, and was confirmed by the present inventors for the first time.

An aspect of the present invention is to provide a method for producing astrocytes, comprising obtaining neural progenitor cells from stem cells followed by differentiating the neural progenitor cells into astrocytes.

As used herein, the term "stem cell" refers to a cell capable of differentiating into two or more new cells while having an ability to self-replicate. The stem cells can be divided into totipotent stem cells, pluripotent stem cells, and multipotent stem cells in accordance with differentiation potency, and into mesenchymal stem cells, embryonic stem cells, and induced pluripotent stem cells in accordance with the tissue from which the stem cells are derived.

In the present invention, the stem cells can be understood to be differentiated into the astrocytes provided in the present invention, where the stem cells can be differentiated into the astrocytes sequentially via embryoid bodies, rosettes, neurospheres, and neural progenitor cells.

Therefore, in the present invention, if differentiation into the astrocytes is possible, all types of stem cells such as mesenchymal stem cells, embryonic stem cells, and induced pluripotent stem cells, specifically, embryonic stem cells, induced pluripotent stem cells, or mesenchymal stem cells derived from bone marrow, adipose tissue, teeth, dental tissues, blood, umbilical cord blood, liver, skin, gastrointestinal tract, placenta, uterus, and fetus, can be used.

In a specific exemplary embodiment of the present invention, the embryonic stem cells were used as the stem cells for obtaining astrocytes, and the embryonic stem cells, while co-culturing with the fibroblasts, were cultured in a culture medium containing basic fibroblast growth factor (bFGF), which induces proliferation and differentiation inhibition of the stem cells.

As used herein, the term "embryoid body", also known as a gemma cup, refers to a ball-like aggregate of the stem cells during early stages of cell division. The embryoid bodies exhibit similar pluripotency to conventional embryonic stem cells and thus can differentiate into bone cells, muscle cells, nerve cells, epithelial cells, fiber cells, and various other biological tissues.

In the present invention, the embryoid bodies can be used as an intermediate mediator for differentiating stem cells into the neural progenitor cells, and can be obtained by culturing the stem cells in a conventional culture medium (e.g., DMEM/F12, KO-DMEM/F12, etc.) comprising various ingredients (e.g., blood serum, non-essential amino acids (NEAA), antibiotics, LDN193189, SB431542, etc.). Time for culturing to form the embryoid bodies from the stem cells is not particularly limited, but may be specifically 2 day to 10 days, more specifically 3 days to 7 days, and most specifically 4 days.

In a specific exemplary embodiment of the present invention, the embryoid stem cells were cultured for 4 days to obtain the embryoid bodies.

As used herein, the term "neural progenitor cells", also known as "neuron precursor cells", broadly refers to all cells that can differentiate into neurons or exist in the differentiation process. Neural stem cells or other stem cells are differentiated to form neuroblasts, and the formed neuroblasts move to sites where neural tubes or neurons are formed, and are then morphologically and functionally differentiated to form axons and dendrites to ultimately form neurons. All cells undergoing differentiation, from stem cells until just before completion of differentiation, correspond to a wide range of the neural progenitor cells, whereas in a narrower range, neuroblasts that have completed differentiation correspond to the neural progenitor cells.

To obtain the neural progenitor cells from the embryoid bodies in vitro, the embryoid bodies are cultured in a culture medium for forming rosettes to obtain the rosettes, and then the collected rosettes are cultured in the same culture medium to obtain the neurospheres, followed by culturing the neurospheres in a culture medium for neural progenitor cells.

Additionally, the culture medium for forming rosettes refers to a culture medium in which the rosettes can be formed from the embryoid bodies, and is not limited as long as the rosettes can be obtained by culturing the embryoid bodies, but may be specifically a culture medium comprising N2, B27™, basic fibroblast growth factor (bFGF), and SHH, more specifically DMEM/F12 or KO-DMEM/F12 comprising N2, B27™, bFGF, and SHH.

Additionally, the culture medium for neural progenitor cells in the present invention refers to a culture medium capable of forming the neural progenitor cells from the neurospheres. As long as the neural progenitor cells can be obtained by culturing the neurospheres therein, the culture medium for neural progenitor cells may be a serum-free medium, but is not limited thereto.

Additionally, time required for culturing to obtain the rosettes from the embryoid bodies is not particularly limited, but may be specifically 4 days to 10 days, more specifically 5 days to 8 days, and most specifically 7 days.

Additionally, time required for culturing to obtain the neurospheres from the rosettes is not particularly limited, but may be specifically 1 days to 5 days, more specifically 2 days to 4 days, and most specifically 3 days.

Additionally, time required for culturing to obtain the neural progenitor cells from the neurospheres is not particularly limited, but may be specifically 1 day to 5 days, more specifically 1 day to 3 days, and most specifically 2 days.

As used herein, the term "rosette" refers to a cell aggregate obtained by culturing the embryoid bodies in the culture medium for inducing neural differentiation comprising a neuron differentiation-inducing component, where the cells are bonded in the form of a flower. The rosette can be understood as an intermediate cell in which a gene required for the differentiation from stem cells to neurons is expressed, thereby accompanying a morphological change. Additionally, accumulation of the rosettes is required to form the neurospheres from the rosettes more effectively, and therefore, it is preferable that as soon as the rosettes are formed, the rosettes are inoculated in a culture dish for high density and then cultured.

As used herein, the term "astrocytes", also known as astroglia, refer to the most common cells of the nervous system, and play a role in aiding neuronal activities while appropriately eliminate neurotransmitters secreted by neurons and controlling ion concentrations in the brain. Recently, astrocytes have been revealed to play certain roles, such as in synapse formation of neurons, regulation of synapse number, and synaptic plasticity, and in the onset of degenerative nervous system diseases as well as differentiation of neural stem cells into nerves and improvement of immune functions. In particular, if a pathogen is infected in a living body and the brain recognizes it, the amount of secretion of various cytokines is increased. The secreted cytokines are known to make the astrocytes perform functions of macrophages by activating the astrocytes, thereby improving immune function.

In the present invention, the astrocytes can be produced by a first culturing in which the neural progenitor cells are cultured in a first culture medium for differentiation into astrocytes, followed by a second culturing in which the first-cultured cells are cultured in a second culture medium for differentiation into astrocytes.

The first culture medium is not limited as long as the astrocytes can be obtained by culturing the neural progenitor cells, but may be a culture medium for forming rosettes containing nonessential amino acids (NEAA), heparin, and epidermal growth factor (EGF).

Additionally, the second culture medium is not limited as long as the astrocytes can be obtained by culturing the first-cultured cells, but may be a conventional culture medium containing ciliary neurotrophic factor (CNTF), activin A, heregulin 1β, insulin-like growth factor 1 (IGF1), and bFGF, more specifically DMEM/F12 or KO-DMEM/F12 containing CNTF, activin A, heregulin 1β, insulin-like growth factor 1 (IGF1), and bFGF.

The IGF1 includes all analogs that have an activity similar to that of IGF1 (e.g., mecasermin, etc.).

Time required for the first differentiation is not limited, but may be specifically 2 day to 10 days, more specifically 3 days to 7 days, and most specifically 5 days, whereas time required for the second differentiation is not limited, but may be specifically 15 day to 30 days, more specifically 20 days to 26 days, and most specifically 23 days.

Therefore, specifically 17 days to 40 days, more specifically 23 days to 33 days, and most specifically 28 days after inoculating and culturing the neural progenitor cells into the culture medium for differentiation into astrocytes, the astrocytes can be obtained.

Using the method of the present invention can not only produce the astrocytes with high purity, but also continuously produce the astrocytes with the same traits using the neural progenitor cells that can be cryopreserved. This is advantageous in that by simply repeating the process of differentiating and producing the astrocytes from the neural progenitor cells, time required for producing the astrocytes can be shortened. In the case where the astrocytes produced in the present invention are transplanted to a patient with a neurodegenerative disease or lowered immune function to treat or improve said diseases, astrocytes that meet an in vivo condition of a patient must be used. Continuous transplantation of the astrocytes may be required to be on a cycle depending on symptoms of the patient. In said case, if the astrocytes first used and those subsequently used show different traits, there is a problem in that the chances of treating said disease may decrease sharply, and thus astrocytes with the same traits must be used. However, maintaining the first-used cholinergic neurons until the treatment is finished is known to be substantially impossible. Nonetheless, using the method provided in the present invention maintains the neural progenitor cells that can be differentiated into the astrocytes and uses the neural progenitor cells to produce the astrocytes of the same traits until treatment of patients is completed, thereby improving a treatment success rate of said disease significantly.

Additionally, there is an advantage in that by repeating the process of differentiating and producing the astrocytes from neural progenitor cells which can be cryopreserved, time required for producing the astrocytes can be shortened, compared to the conventional technique for astrocytes production.

As a specific example of the method for producing the astrocytes provided in the present invention, the method for producing the astrocytes of the present invention may comprise:

(a) obtaining embryoid bodies by culturing the stem cells;

(b) obtaining neurospheres by culturing the embryoid bodies;

(c) obtaining the neural progenitor cells by culturing the neurospheres; and (d) obtaining astrocytes by culturing the neural progenitor cells in a culture medium for differentiation into astrocytes in two steps, but is not limited thereto.

Additionally, in the present invention, step (b) may comprise obtaining rosettes by culturing the embryoid bodies in the culture medium for forming rosettes, followed by obtaining the neurospheres by culturing the rosettes, but is not limited thereto.

Furthermore, step (d) in the present invention specifically may comprise:

(d1) first culturing the neural progenitor cells in the first culture medium for differentiation into astrocytes; and (d2) second culturing the first cultured cells in the second culture medium for differentiation into astrocytes, but is not limited thereto.

As described above, the stem cells of step (a) may be mesenchymal stem cells, embryonic stem cells, or induced pluripotent stem cells; the stem cells of step (a) may be cultured in DMEM/F12 comprising blood serum, non-essential amino acids (NEAA), antibiotics, LDN193189, and SB431542 for 2 days to 10 days to form the embryoid bodies; in step (b), the embryoid bodies are cultured in a culture medium for forming rosettes (a conventional culture medium comprising N2, B-27™, bFGF, etc.) for 4 days to 10 days to obtain the rosettes, and the obtained rosettes are cultured in the same culture medium for 2 days to 5 days to obtain the neurospheres; in step (c), the neurospheres are cultured in a culture medium for neural progenitor cells (e.g., a culture medium comprising serum (e.g., FBS)) for 1 day to 5 days to obtain the neural progenitor cells, and the obtained neural progenitor cells are cryopreserved and thus can be used in repeatedly reproducing the astrocytes with the same traits; and in step (d), the neural progenitor cells are cultured in the first culture medium for differentiation into astrocytes (a culture medium for forming rosettes comprising NEAA, heparin, and EGF) for 2 days to 10 days, and then are cultured in the second culture medium for differentiation into astrocytes (StemPro hESC SFM comprising CN Activin A, Heregulin 1β, IGF1 analog, and bFGF) for 15 days to 30 days to obtain the astrocytes.

According to a specific exemplary embodiment, the embryonic stem cells are cultured to obtain the embryoid bodies, and the obtained embryoid bodies are cultured to obtain rosettes. The rosettes are collected and then cultured again to obtain the neurospheres. The neurospheres are cultured in the two culture media for differentiation into astrocytes to produce the astrocytes.

As an aspect to achieve the above object, the present invention provides astrocytes prepared by the method for preparing astrocytes described above.

The astrocytes provided in the present invention contain other cells excluding the astrocytes in a significantly low amount, compared to the astrocytes produced by the conventional preparation method, thereby significantly increasing purity of the astrocytes. The astrocytes of the present invention can improve therapeutic efficiency of patients with a disease that require transplantation of the astrocytes.

MODE FOR INVENTION

Hereinbelow, the present invention will be described in detail with accompanying exemplary embodiments. However, the exemplary embodiments disclosed herein are only for describing the invention more specifically and should not be construed as limiting the scope of the present invention.

Example 1: Production of Astrocytes

Example 1-1: hES (human Embryonic Stem Cell) Culture

In DMEM/F12 that can inhibit proliferation of the embryonic stem cells, comprising 20 ng/mL of basic fibroblast growth factor (bFGF), 20% KnockOut™ Serum Replacement, NEAA, and β-mercaptoethanol, a human embryonic stem cell line (H9) was co-cultured with an embryo fibroblast (mouse MEF) of a mouse that stopped growing via γ-ray irradiation, and was subcultured for 6 days with daily replacement of the culture medium.

Example 1-2: Obtaining of Embryoid Bodies

The human embryonic stem cells cultured in Example 1-1 were cut in a size of 250 μm$^2$ and were inoculated in the DMEM/F12 containing 20% KnockOut™ Serum Replacement, 100 nM of LDN193189, and 10 μM of SB431542, and then cultured for 4 days with daily replacement of the culture medium to obtain the embryoid bodies.

Example 1-3: Obtaining of Neurospheres

In a culture dish coated with Matrigel™ (50 μL/cm$^2$; BD), the embryoid bodies obtained in Example 1-2 were inoculated in a culture medium for forming rosettes (DMEM/F12 comprising 100×N2, 50×B27™, and 20 ng/mL of bFGF) and were cultured for 7 days with replacement of the culture medium every 2 days to obtain flame-shaped rosettes. The rosettes were collected and inoculated in the same culture medium, and then were suspension-cultured for 3 days to obtain the neurospheres.

Example 1-4: Obtaining of Neural Progenitor Cell (NPC)

The neurospheres obtained in Example 1-3 were treated with Accutage™ (inactive cell technologies) to obtain single cells, and the obtained single cells were inoculated into StemCell™'s Neural Progenitor culture medium (STEMdiff™) (distributed by StemCell Technologies, Vancouver, British Columbia, Canada), and were then cultured in a culture dish coated with Matrigel™ (50 μL/cm$^2$; BD) for 2 days to obtain the neural progenitor cells.

Example 1-5: Production of Astrocytes

The neural progenitor cells obtained in Example 1-4 were inoculated in a culture dish coated with Matrigel™ (50 μL/cm$^2$; BD) and were then cultured with the first culture medium for differentiation into astrocytes (a culture medium for forming rosettes comprising (100×NEAA, 5 μg/mL of Heparin, and 20 ng/mL of EGF) for 5 days with replacement of the culture medium every 2 days to obtain the intermediate cells between the neural progenitor cells and the astrocytes. The obtained intermediate cells were inoculated in the second culture medium for differentiation into astrocytes (StemPro hESC SFM comprising 10 ng/mL of CNTF, 10 ng/mL of Activin A, 10 ng/mL of Heregulin 1β, 200 ng/mL of IGF1 analog, and 8 ng/mL of bFGF) and were cultured for 23 days with replacement of the culture medium every 2 days to obtain the astrocytes (FIG. 1).

Example 2: Verification of Efficiency of Differentiation into Astrocytes

Example 2-1: Comparison of Astrocyte Production Rates in Relation to Differentiation Time In regard to Example 1-5, during the process in which where the neural progenitor cells are cultured in the first and second culture media for differentiation into astrocytes for 28 days, the cultured cells were aliquoted at the 5$^{th}$, 10$^{th}$, 14$^{th}$, 17$^{th}$, 21$^{st}$, and 28$^{th}$ days of the differentiation. The immunofluorescent staining was conducted on each of the aliquoted cells using the neuronal marker (MAP2) and astrocyte marker (GFAP) to compare production rates of neurons and astrocytes according to differentiation time (FIG. 2).

Figure 2:
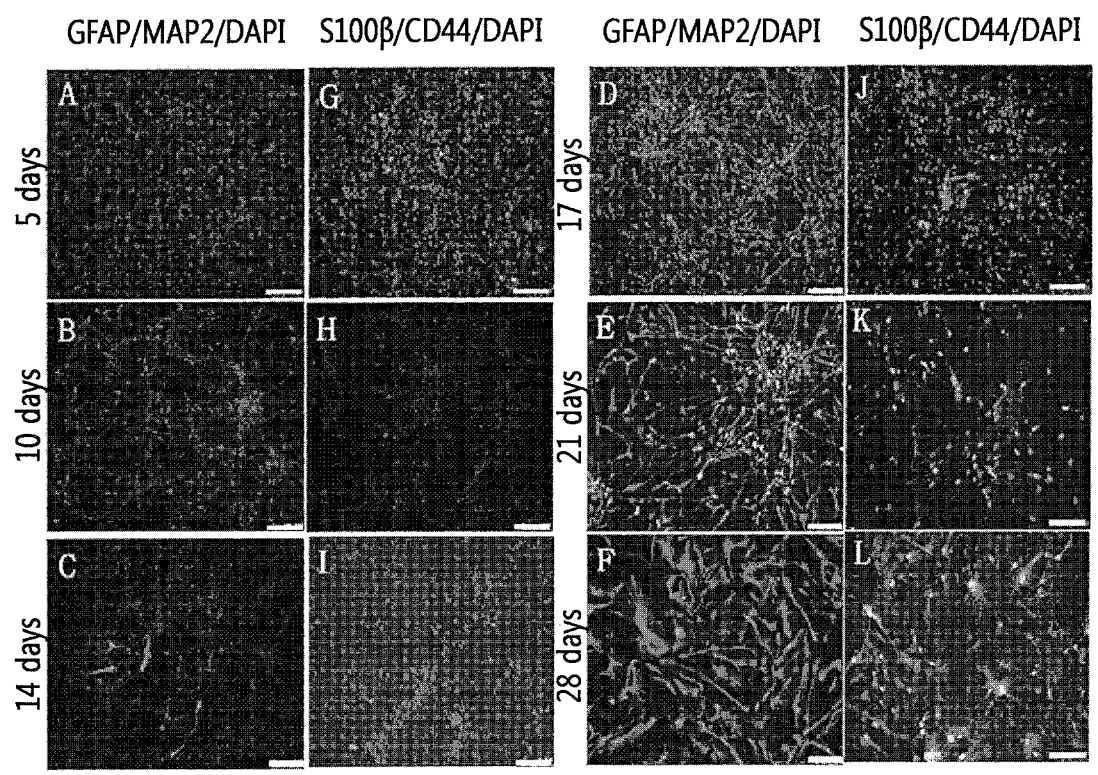
FIG. 2 is photomicrographs showing the results of immunofluorescent staining on the culture cells of 5, 10, 14, 17, 21, and 28 days of differentiation in the culture media for the first and second differentiating into astrocytes for 28 days using a neuronal marker (MAP2) and an astrocyte marker (GFAP).

As shown in FIG. 2, the neuronal markers were observed after 5 days, and were the majority after 10 days. However, the astrocytes started to be observed after 14 days. A proportion of the astrocyte marker increased over time, whereas that of the neuronal marker decreased. After 28 days, only the astrocyte markers were observed, but not the neuronal marker. As shown in FIG. 2 as well, it took 28 days total to obtain the astrocyte from the neural progenitor cells, and this refers to a reduction of the time required for the astrocyte production over the conventional method. In other words, as it is known that according to the conventional method of differentiation the astrocytes from the neural progenitor cells (Stem Cells 2013; 31:941-952), astrocytes can be obtained in a case where the neural progenitor cells were inoculated in a culture medium for differentiation into astrocytes (StemPro hESC SFM containing 10 ng/mL of Activin A, 10 ng/mL of Heregulin 1β, and 200 ng/mL of IGF1 analog) in a culture dish coated with fibronectin and were cultured for more than 35 days, it was found that using the method of the present invention has an effect of shortening the culturing time of about 7 days.

Example 2-2: Flow Cytometry

Immunofluorescent staining was carried out using an antibody against CD44 which is one of astrocyte markers for the astrocytes that were cultured for 28 days in Example 1-5. Ratios of the astrocytes labeled with CD44-stained cells were measured by carrying out the flow cytometry (FITC) using the stained cells (FIG. 3).

Figure 3:
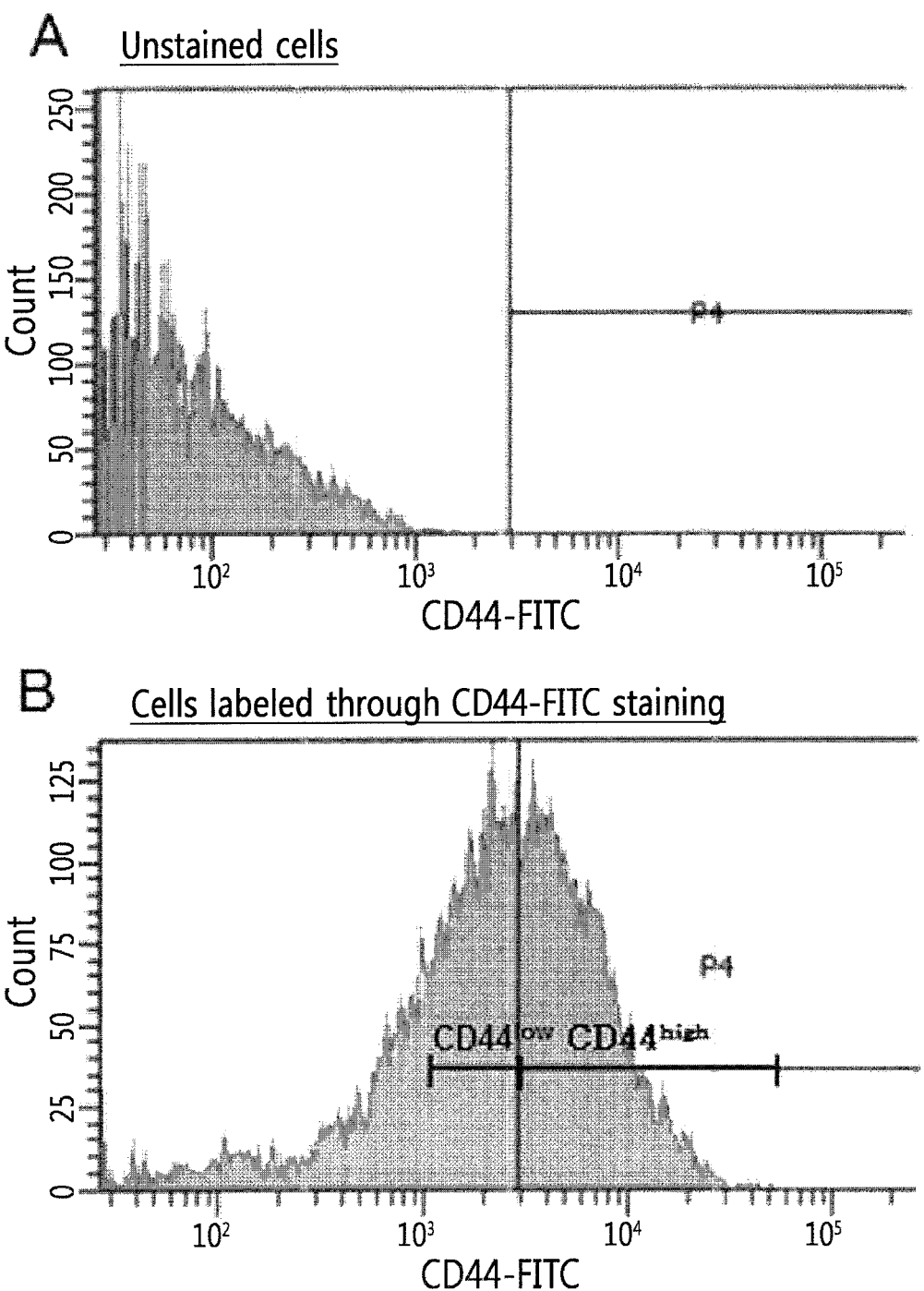
FIG. 3 is graphs showing the results of measurements of proportions of the astrocytes differentiated and obtained from the neural progenitor cells using flow cytometry.

As shown in FIG. 3, about 93% of effective cells differentiated from the neural progenitor cells were confirmed to be astrocytes.

According to what has been reported so far, it is known that more than 90% of GFAP is expressed after culturing the stem cells for 24 to 25 weeks (Nature Protocol, 2011; 6(11):1710-1717), and it is also known that maximum of 80% of the stem cells can be differentiated into the astrocytes after culturing for 35 days to 42 days (Stem Cells, 2013; 31:941-952).

In contrast, however, the method for preparing the astrocytes of the present invention can not only shorten a time for differentiation into astrocytes, but also show a significantly high proportion of the differentiated astrocytes to the stem cells used at the beginning.

Therefore, using the method for producing the astrocytes provided by the present invention enables a rapid differentiation and production of the astrocytes from the stem cells with high efficiency and purity.

From the foregoing, a skilled person in the art to which the present invention pertains will be able to understand that the present invention may be embodied in other specific forms without modifying the technical concepts or essential characteristics of the present invention. In this regard, the exemplary embodiments disclosed herein are only for illustrative purposes and should not be construed as limiting the scope of the present invention. On the contrary, the present invention is intended to cover not only the exemplary embodiments but also various alternatives, modifications, equivalents, and other embodiments that may be included within the spirit and scope of the present invention as defined by the appended claims.

What is claimed is:

1. A method for preparing astrocytes comprising (A) culturing stem cells under conditions so as to form neural progenitor cells and (B) treating the neural progenitor cells so as to form astrocytes,
    wherein in (A) the method comprises:
    (a) culturing the stem cells in a medium comprising blood serum, non-essential amino acids (NEAA), antibiotics, LDN193189, and SB431542 to obtain embryoid bodies from the stem cells;
    (b) culturing the embryoid bodies from (a) in a medium comprising N2, B-27™, and basic fibroblast growth factor (bFGF) to obtain rosettes and suspension-culturing the rosettes in the same culture medium to obtain the neurospheres; and
    (c) culturing the neurospheres in STEMdiff™ Neural Progenitor Medium to form neural progenitor cells,
    wherein the treatment of the neural progenitor cells to form astrocytes comprises two culturing steps, wherein the two culturing steps comprise:
    i) culturing the neural progenitor cells in a first culture medium; and then
    ii) culturing the resulting cells in a second culture medium
    wherein the first culture medium comprises non-essential amino acids, heparin, and epidermal growth factor (EGF), and the second culture medium comprises ciliary neurotrophic factor (CNTF), activin A, heregulin 1β, insulin-like growth factor 1 (IGF1) and bFGF.

2. The method according to claim 1, wherein the stem cells in (A)(a) are mesenchymal stem cells, embryonic stem cells, or induced pluripotent stem cells.

3. The method according to claim 1, wherein the medium in (A)(b) is either DMEM/F12 or KO-DMEM/F12.

4. The method according to claim 1, wherein the culturing in step (B)(i) is performed for 2 days to 10 days.

5. The method according to claim 1, wherein the culturing in (B)(ii) is performed for 15 days to 30 days.

6. The method according to claim 1, wherein
    the method comprises in (A):
    (a) obtaining embryoid bodies by culturing the stem cells for 2 days to 10 days;
    (b) obtaining rosettes by culturing the embryoid bodies in a culture medium for 4 days to 10 days and then obtaining neurospheres by culturing the rosettes for 1 day to 5 days;
    (c) obtaining the neural progenitor cells by culturing the neurospheres for 1 day to 5 days;
    and in (B):
    (i) first culturing the neural progenitor cells in the first culture medium for 2 days to 10 days; and
    (ii) culturing the resulting cells in the second culture medium for 15 days to 30 days
wherein the culture medium in (A)(b) is DMEM/F12 or KO-DMEM/F12.

* * * * *